US00PP25701P2

(12) United States Plant Patent
Jackson et al.

(10) Patent No.: US PP25,701 P2
(45) Date of Patent: Jul. 14, 2015

(54) ***CERCIS* TREE NAMED 'JN7'**

(50) Latin Name: *Cercis canadensis*
Varietal Denomination: JN7

(71) Applicants: Ray Jackson, Belvidere, TN (US); Cindy Jackson, Belvidere, TN (US)

(72) Inventors: Ray Jackson, Belvidere, TN (US); Cindy Jackson, Belvidere, TN (US)

( * ) Notice: Subject to any disclaimer, the term of this patent is extended or adjusted under 35 U.S.C. 154(b) by 85 days.

(21) Appl. No.: 13/987,781

(22) Filed: Aug. 31, 2013

(51) Int. Cl.
*A01H 5/00* (2006.01)

(52) U.S. Cl.
USPC ..... Plt./216

(58) Field of Classification Search
USPC ..... Plt./216
CPC ..... A01H 5/02; A01H 5/00
See application file for complete search history.

*Primary Examiner* — Kent L Bell
(74) *Attorney, Agent, or Firm* — C. A. Whealy

(57) ABSTRACT

A new and distinct cultivar of *Cercis* tree named 'JN7', characterized by its upright vase-shaped plant habit with relatively narrow branching angle; vigorous growth habit; and good garden performance.

3 Drawing Sheets

Botanical designation: *Cercis canadensis*.
Cultivar denomination: 'JN7'.

BACKGROUND OF THE INVENTION

The present invention relates to a new and distinct *Cercis* plant, botanically known as *Cercis canadensis*, commercially referred to as Eastern Redbud and hereinafter referred to by the name 'JN7'.

The new *Cercis* plant originated from an open-pollination in Belvidere, Tenn. of an unidentified proprietary selection of *Cercis canadensis*, not patented, as the female, or seed, parent with an unknown selection of *Cercis canadensis* as the male, or pollen, parent. The new *Cercis* plant was discovered and selected by the Inventors as a single plant within the progeny of the stated open-pollination in a controlled nursery environment in Belvidere, Tenn. in the fall of 2007.

Asexual reproduction of the new *Cercis* plant by bud grafting onto a proprietary seedling *Cercis* rootstock in a controlled environment in Belvidere, Tenn. since 2008 has shown that the unique features of this new *Cercis* plant are stable and reproduced true to type in successive generations.

SUMMARY OF THE INVENTION

Plants of the new *Cercis* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'JN7'. These characteristics in combination distinguish 'JN7' as a new and distinct *Cercis* plant:

1. Upright vase-shaped plant habit with relatively narrow branching angle.
2. Vigorous growth habit.
3. Good garden performance.

Plants of the new *Cercis* can be compared to plants of the female parent selection. Plants of the new *Cercis* differ primarily from plants of the female parent selection in plant habit as plants of the female parent selection are flat-topped to rounded in overall shape. In addition, plants of the new *Cercis* are more uniform than plants of the female parent selection.

Plants of the new *Cercis* can also be compared to plants of *Cercis canadensis* 'Greswan', disclosed in U.S. Plant Pat. No. 19,654. In side-by-side comparisons, plants of the new *Cercis* differed primarily from plants of 'Greswan' in the following characteristics:

1. Plants of the new *Cercis* had an upright vase-shaped plant habit whereas plants of 'Greswan' were upright and outwardly arching.
2. Branch angle for plant of the new *Cercis* was about 45° from vertical whereas branch angle for plants of 'Greswan' was about 60° from vertical.
3. Plants of the new *Cercis* were more vigorous and grew faster than plants of 'Greswan'.

BRIEF DESCRIPTION OF THE PHOTOGRAPHS

The accompanying colored photographs illustrate the overall appearance of the new *Cercis* plant showing the colors as true as it is reasonably possible to obtain in colored reproductions of this type. Colors in the photographs may differ slightly from the color values cited in the detailed botanical description which accurately describe the colors of the new *Cercis* plant.

The photograph on the first sheet is a side perspective view of a typical tree of 'JN7'.

The photograph on the second sheet is a side perspective view of a typical flowering tree of 'JN7'.

The photograph on the third sheet is a close-up view of a typical tree of 'JN7'.

DETAILED BOTANICAL DESCRIPTION

The aforementioned photographs and following observations, measurements and values describe trees grown during the spring in seven-gallon containers in an outdoor nursery in Park Hill, Okla. and under cultural practices typical of commercial *Cercis* production. During the production of the plants, day temperatures averaged 22° C. and night temperatures averaged 9° C. Plants used for the photographs were six years old and plants used for the description were three years old. In the description, color references are made to The Royal Horticultural Society Colour Chart, 2001 Edition, except where general terms of ordinary dictionary significance are used.

Botanical classification: *Cercis canadensis* 'JN7'.

Parentage:

*Female, or seed, parent*.—Unidentified proprietary selection of *Cercis canadensis*, not patented.

*Male, or pollen, parent*.—Unknown selection of *Cercis canadensis*, not patented.

Propagation:

*Type*.—Bud-grafted onto a proprietary seedling *Cercis* rootstock.

*Root description*.—Medium in thickness, fibrous; brown, close to N199B, in color.

*Rooting habit*.—Moderately freely branching; medium density.

Plant description:

*Plant and growth habit*.—Deciduous tree; upright and narrow vase-shaped plant habit; vigorous growth habit and rapid growth rate; freely branching habit.

*Plant height*.—About 6 meters to 7.5 meters.

*Plant diameter* (*area of spread*).—About 2.8 meters.

Lateral branch description:

*Length*.—Variable depending on position on the tree.

*Diameter*.—About 9 mm.

*Internode length*.—About 1.5 cm to 5 cm.

*Aspect*.—Relatively narrow, about 45° from vertical.

*Strength*.—Very strong.

*Texture*.—Smooth, glabrous.

*Color*.—Close to 146A.

Leaf description:

*Arrangement*.—Alternate, single.

*Length*.—About 13.6 cm.

*Width*.—About 13.6 cm.

*Shape*.—Cordate to reniform.

*Apex*.—Acute to obtuse.

*Base*.—Cordate.

*Margin*.—Entire.

*Texture, upper and lower surfaces*.—Smooth, glabrous.

*Venation pattern*.—Palmate.

*Color*.—Developing leaves, upper surface: Close to 139A. Developing leaves, lower surface: Close to 143A. Fully expanded leaves, upper surface: Close to 137A; venation, close to N144D. Fully expanded leaves, lower surface: Close to 138B; venation, close to 145A.

*Petioles*.—Length: About 5 mm. Diameter: About 2 mm. Texture, upper and lower surfaces: Smooth, glabrous. Color, upper surface: Close to 143A. Color, lower surface: Close to 144B.

Flower description:

*Flower arrangement and flowering habit*.—Single flowers arranged in terminal and axillary clusters with about two to six flowers per cluster; freely flowering habit; flowers face mostly outwardly.

*Natural flowering season*.—Early flowering habit, plants of the new *Cercis* flower in the early to mid-spring in Oklahoma.

*Flower longevity*.—Flowers last about two to three weeks on the plant; flowers not persistent.

*Fragrance*.—None detected.

*Flower diameter*.—About 1.3 cm.

*Flower length*.—About 1 cm.

*Flower depth*.—About 1.5 cm.

*Flower buds*.—Length: About 5 mm. Diameter: About 2 mm. Shape: Conical. Color: Close to 82A to 82B; towards the base, close to N77A.

*Petals*.—Arrangement: Typically five petals in a single whorl. Length: About 5 mm. Width: About 3 mm. Shape: Oblong. Apex: Acute. Base: Obtuse. Margin: Entire. Texture: Smooth, glabrous. Color: When opening, upper and lower surfaces: Close to 77B. Fully opened, upper and lower surfaces: Close to 75A; color becoming closer to 75D with development.

*Sepals*.—Arrangement: Typically five sepals fused forming a cup-shaped, blunt-toothed calyx. Calyx length: About 4 mm to 5 mm. Calyx width: About 5 mm to 6 mm. Sepal texture, upper and lower surfaces: Smooth, glabrous. Sepal color, upper and lower surfaces: Close to N79B.

*Peduncles*.—Length: About 2 cm. Diameter: About 1 mm. Strength: Strong. Texture: Pubescent. Color: Close to 137B.

*Pedicels*.—Length: About 1.8 mm. Diameter: About 1 mm. Strength: Strong. Texture: Smooth, glabrous. Color: Close to 79A.

*Reproductive organs*.—Androecium: Stamen number: About ten per flower. Filament length: About 1 cm. Filament color: Close to 69C. Anther shape: Round to slightly oblong. Anther length: About 1 mm. Anther color: Close to 200B. Amount of pollen: Abundant. Pollen color: Close to 161A. Gynoecium: Pistil number: One per flower. Pistil length: About 1 cm. Style length: About 1 mm. Style color: Close to 71C. Stigma shape: Elliptical. Stigma color: Close to 145C. Ovary color: Close to 137B.

*Seeds and fruits*.—Seed and fruit development have not been observed on plants of the new *Cercis*.

Garden performance: Plants of the new *Cercis* have been observed to have good garden performance and to tolerate wind, rain and temperatures ranging from about −29° C. to about 43° C.

Pathogen & pest resistance: Plants of the new *Cercis* have not been observed to be resistant to pathogens and pests common to *Cercis* plants.

It is claimed:

1. A new and distinct *Cercis* tree named 'JN7' as illustrated and described.

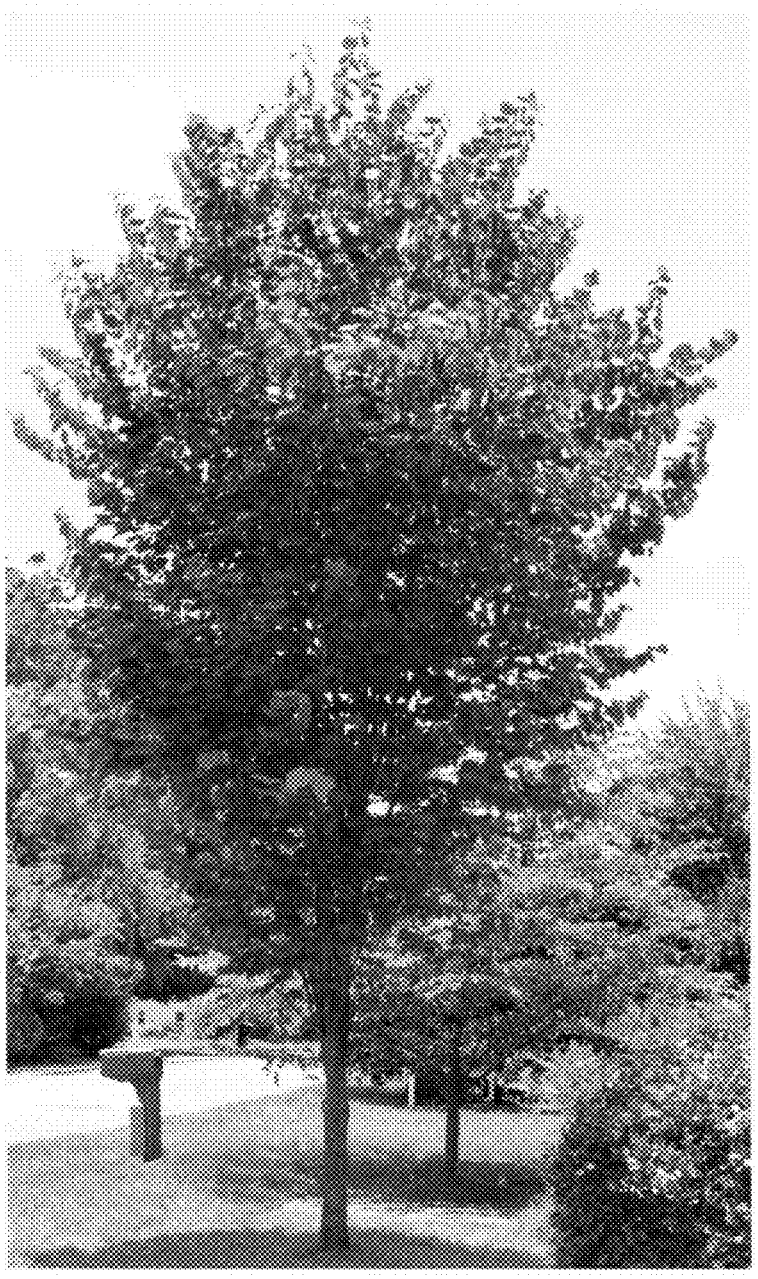

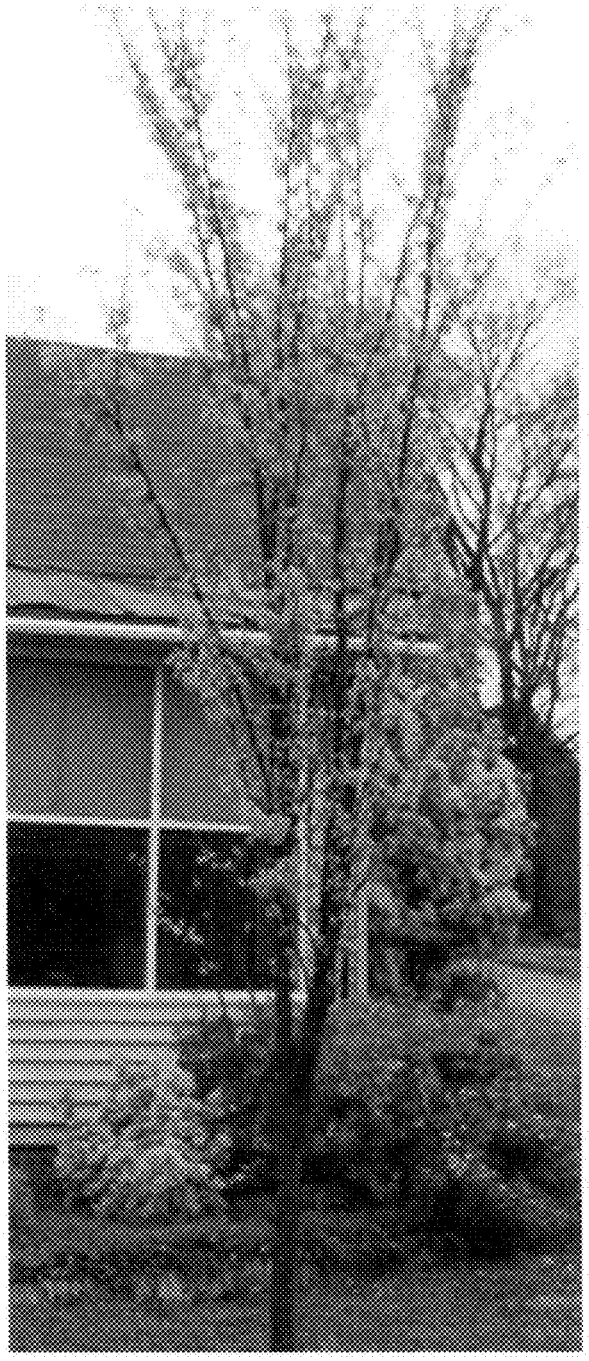

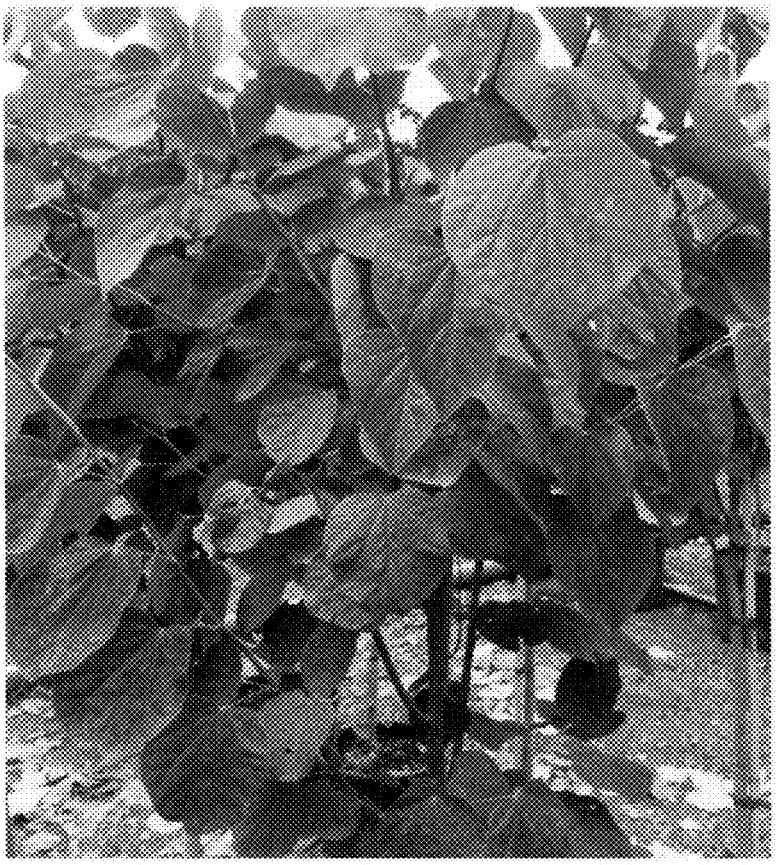

* * * * *